US011116983B2

(12) United States Patent
von Arx et al.

(10) Patent No.: US 11,116,983 B2
(45) Date of Patent: Sep. 14, 2021

(54) IMPLANTABLE MEDICAL DEVICES AND SYSTEMS WITH COMMUNICATION/SENSING BASED ON NEAR INFRARED SIGNALS

(71) Applicant: BIOTRONIK SE & Co. KG, Berlin (DE)

(72) Inventors: Jeffrey A. von Arx, Lake Oswego, OR (US); Brian M. Taff, Portland, OR (US); Kurt Swenson, Dayton, OR (US); Joseph Simon Raven, Tigard, OR (US); Yu Wang, Lake Oswego, OR (US); Paul Stadnik, Lake Oswego, OR (US); Ulrich Hugel, Hillsboro, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 93 days.

(21) Appl. No.: 16/597,067

(22) Filed: Oct. 9, 2019

(65) Prior Publication Data

US 2021/0106833 A1  Apr. 15, 2021

(51) Int. Cl.
*A61N 1/37* (2006.01)
*A61B 5/00* (2006.01)
*A61N 1/372* (2006.01)
*A61N 1/375* (2006.01)
*A61N 5/06* (2006.01)

(52) U.S. Cl.
CPC .......... *A61N 1/3706* (2013.01); *A61B 5/0031* (2013.01); *A61N 1/3756* (2013.01); *A61N 1/37247* (2013.01); *A61N 2005/0659* (2013.01)

(58) Field of Classification Search
CPC .............. A61N 1/3706; A61N 1/37247; A61N 1/3756; A61N 2005/0659; A61B 5/0031
USPC ........................................................ 607/30
See application file for complete search history.

(56) References Cited

U.S. PATENT DOCUMENTS

| | | | |
|---|---|---|---|
| 2009/0248106 A1* | 10/2009 | Black | A61N 1/3787 607/33 |
| 2014/0135647 A1* | 5/2014 | Wolf, II | A61B 5/0031 600/561 |
| 2015/0174412 A1 | 6/2015 | Stahmann et al. | |
| 2015/0202456 A1* | 7/2015 | Andersen | A61N 5/0601 604/20 |
| 2015/0321012 A1 | 11/2015 | Cinbis et al. | |
| 2018/0140848 A1* | 5/2018 | Stahmann | A61N 1/36507 |
| 2018/0185660 A1 | 7/2018 | Eddy et al. | |
| 2019/0143127 A1 | 5/2019 | Winkler et al. | |

(Continued)

FOREIGN PATENT DOCUMENTS

WO    20150038352 A1    3/2015

OTHER PUBLICATIONS

European Search Report and Annex to the European Search Report on European Patent Application No. EP 19 20 7044.9, dated May 28, 2020 (6 pages).

(Continued)

*Primary Examiner* — Erin M Piateski
(74) *Attorney, Agent, or Firm* — Buchanan Ingersoll & Rooney PC

(57) ABSTRACT

Technology for near infrared (NIR) based communication and/or sensing of implantable medical devices and systems as well as method of operating the same.

6 Claims, 5 Drawing Sheets

(56) References Cited

U.S. PATENT DOCUMENTS

2019/0336077 A1* 11/2019 Kuhn ................ A61B 5/14546

OTHER PUBLICATIONS

Friebel et. al. "Influence of oxygen saturation on the optical scattering properties of human red blood cells in the spectral range 250 to 2,000 nm", J. of Biomed. Optics 14 (2009).

Jacques, "Optical properties of biological tissues: a review", Phys. Med. Biol. 58 (2013) R37-R61.

M. Friebel et. al. "Influence of oxygen saturation on the optical scattering properties of human red blood cells in the spectral range 250 to 2,000 nm", Journal of Biomedical Optics, vol. 14(3), 034001 (May/Jun. 2009) (pp. 1-6).

* cited by examiner

IMPLANTABLE MEDICAL DEVICES AND SYSTEMS WITH COMMUNICATION/SENSING BASED ON NEAR INFRARED SIGNALS

TECHNICAL FIELD

The present disclosure relates to implantable medical devices and systems with communication/sensing based on near infrared signals and to methods for operating such systems and devices. In particular, the present disclosure relates to embodiments of a multi-chamber leadless pacemaker system and corresponding operating methods.

BACKGROUND

In recent years, leadless pacemakers have become increasingly important in cardiac rhythm management. Leadless pacemakers (LP), in contrast to pacemakers implanted subcutaneously using leads extending transvenously into the heart, avoid leads in that the pacemaker device itself is implanted into the heart, the pacemaker having the shape of a capsule for implantation into cardiac tissue, in particular the right ventricular wall (typically the septum as a preferred site) of the right ventricle. Such leadless pacemakers exhibit the inherent advantage of not using leads, which can reduce risks for the patient involved with leads transvenously accessing the heart, such as the risk of pneumothorax, lead dislodgement, cardiac perforation, venous thrombosis and the like.

LP systems currently available on the market are generally single chamber LP system, i.e., they provide intracardiac pacing in a single heart chamber. For example, an LP device may specifically be designed for implantation in the right ventricle and, in this case, during implant are placed in or on the right ventricular wall. A ventricular pacing may, for example, be indicated in case a dysfunction at the AV node occurs, but the sinus node function is intact and appropriate. In such a case in particular a so-called VDD pacing may be desired, involving a ventricular pacing with atrial tracking and hence requiring a sensing of atrial activity in order to a pace at the ventricle based on intrinsic atrial contractions.

It is generally desirable to provide improved sensing solutions for acquiring, e.g., timing information about the cardiac cycle that can serve as a basis for precisely controlling the intracardiac pacing of an LP device, such as a VDD LP device.

For implementing a VDD Leadless pacemaker, the following sensing solutions are known: Using an accelerometer to sense atrial contraction; using far field electrical sensing to sense atrial contraction; assessing dynamic device electrode impedance variations throughout the cardiac cycle; using heart sounds to sense atrial contraction, atrial filling, and/or valve closure; and using the RV (right ventricle) pressure to sense atrial contraction. All of these approaches lack sensitivity and/or specificity with regard to the sensing results.

In document U.S. Publication No. 2015/0321012, a medical device system is proposed, wherein a physiological signal is sensed by a first device. The first device then generates a control signal in response to the physiological signal, and an optical trigger signal is transmitted in response to the control signal to a second device, which is wholly implantable within a heart chamber. The second device then delivers therapy in response to detecting the optical trigger signal.

Further, for an optimal treatment of many cardiac rhythm deficiencies it would be beneficial to provide for a multi-chamber LP system, wherein multiple LP devices operate in multiple heart chambers (e.g., in two or three heart chambers) and communicate among each other on a beat to beat basis to synchronize their pacing. For this, an ultra-low power intra-body communication scheme is needed.

Conventional solutions for an intra-body implant to implant communication rely, for example, on inductive communication, RF communication (e.g., via MICS or BLE), galvanic communication, or acoustic (ultrasound) communication. Such approaches are, however, not suitable for an efficient and reliable intra-body communication between different LP devices for several reasons: For example, with coil communication, the required communication distances can be achieved only by means of a precise coil alignment, whereas the LP application requires the communication link to work with arbitrary device orientations. RF communication is by far too power consuming to be used as an intra-body communication link for coordinating pacing timing between different LP implants. Galvanic communication, i.e., communicating with sub-threshold charge injection through the same electrodes as the physiological pacing and sensing electrodes, is too complex. This is due to the fact that: 1) Physiological pacing polarizes the electrodes, interfering with their ability to sense galvanic signals, and 2) the communication signal strength must be well below the cardiac capture threshold in order to minimize the risk of capturing the heart with the communication signal. Finally, acoustic communication requires a fairly bulky transducer for transmission and reception, which would complicate the design and increase the costs of the electronics module of an LP device. Further, it would be challenging to coordinate the pacing timing via an acoustic link, which is relatively slow.

In addition, there is generally also a need for a communication between implanted components of an LP system and an external device, such as a clinician's programmer or a patient remote. In many modern active implantable medical devices (AIMDs), these communication use far-field RF communications in either the MICS or 2.4 GHz ISM band. The challenge with these systems is initiating the communications session. Far-field RF takes too much power for the implant to always be listing for a signal, so in most AIMDs the far-field RF system is turned off >98% of the time. In order to use the far-field communications systems a mechanism for coordinated wake-up of the RF sub-system is needed. For example, some known solutions in this respect use a wakeup scheme for a relatively high power implanted transceiver to start a communications session, wherein the wakeup signal is transmitted by means of a coil and a wand, or it is provided that the higher power transceiver wakes up periodically to check for communications initiation.

With regards to waking up an implant to start a communications session, the known solutions have the following drawbacks: In case of relatively high power RF being implemented as the primary communication method between the implantable device and an external device, implementing a secondary communication method such as inductive, acoustic or galvanic communication typically requires additional custom design external devices. Further, the drawback for periodic RF wakeup is a relatively high power consumption and a potential lack of security. The implant must periodically wake up to check for relevant transmissions. There is a power vs. latency tradeoff and any reasonable latency will dramatically increase power consumption due to turning on the implant's receiver. Hence, there is desire for improving the communication between implanted components of an LP system and an external device, e.g., with regard to power efficiency and security.

The present invention is directed at overcoming one or more of the above-mentioned problems.

SUMMARY

It is an object to provide improved technology for communication and/or sensing of implantable medical devices. In particular, a communications solution for an LP system, which is fast, power efficient, reliable and has low physical size (low component count) shall be provided. Further, it is an object to provide an LP device which may operate within such an LP system and/or which has an improved sensing capability for acquiring, e.g., timing information about the cardiac cycle that can serve as a basis for controlling the intracardiac pacing. In addition, it is an object to provide a power efficient and secure solution for the communication between implanted components of a system and an external device.

In a first aspect, a system is provided. The system comprises a first implantable medical device and a second implantable medical device. The first implantable medical device comprises an NIR transceiver (NIR—near infrared). The second implantable medical device comprises an NIR receiver. The NIR receiver is configured to receive an NIR signal transmitted by the NIR transceiver. The NIR receiver may be incorporated in an NIR transceiver. In this case, the first implantable medical device may comprise a first NIR transceiver and the second implantable medical device may comprise a second NIR transceiver, wherein the second NIR transceiver may be configured to receive an NIR signal transmitted by the first NIR transceiver.

The first implantable medical device may comprise a first housing. The NIR transceiver (or the first NIR transceiver) may be arranged in or at the first housing. The second implantable medical device may comprise a second housing. The NIR receiver (or the second NIR transceiver) may be arranged in or at the second housing.

The second implantable medical device may be a first leadless pacemaker device configured to provide intracardiac pacing, wherein the first leadless pacemaker device comprises a first NIR transceiver. The first implantable medical device may be a second leadless pacemaker device configured to provide intracardiac pacing, wherein the second leadless pacemaker device comprises a second NIR transceiver.

Hence, according to an embodiment of the first aspect, an intra-body communication between implanted components of an LP system (LP—leadless pacemaker) may be carried out by means of NIR radiation. It should be noted in this context that NIR light at wavelengths of 650 to 1350 nm penetrates tissue, including blood, reasonably well (so well that research is being done on NIR imaging as a possible low cost alternative to MRI). For example, in deoxygenated blood, which is found in the right side of the heart, the absorption coefficient for NIR light is approximately in the range from 0.4 to 11 cm$^{-1}$ (depending on the exact NIR wavelength), and for oxygenated blood, which is found in the left side of the heart, the absorption coefficient (depending on wavelength) is approximately in the range from 1.7 to 7 cm$^{-1}$ (cf. Jacques, "Optical properties of biological tissues: a review", Phys. Med. Biol. 58 (2013) R37-R61). The absorption coefficient (g) can be used to calculate the surviving fraction of the incident light (T) after traveling a distance L through a medium with the following equation:

$$T = e^{-\mu L} \quad \text{(Equation 1)}$$

Heart muscle and heart valves are also fairly transparent to NIR light, as is most soft human tissue. These absorption coefficients are adequate to allow for low power optical communication and/or signaling (e.g., ping and response interactions) over distances of ~10 cm or more by modulating NIR light sent between two implants (or between an implant and an external device, see below).

For example, the first leadless pacemaker device and the second leadless pacemaker device, when implanted in different heart chambers of a patient, are configured to perform bi-directional chamber-to-chamber communication by means of the first and second NIR transceivers. Thus, a pacing timing may be synchronized among the first and the second LP devices. As a result, the LP system may be configured as a multi-chamber LP system with pacing timing communication based on NIR signals.

In a further development, there may be provided even more (e.g., at least 3) of such LP devices, each comprising an NIR transceiver or at least an NIR receiver or NRI transmitter for communicating pacing timing information among each other.

Further, in an embodiment, the communication may be carried out at wavelengths in the range from 1000 nm to 1200 nm, such as from 1050 nm to 1150 nm, such as at 1100 nm. In other words, the NIR transceiver (or the first NIR transceiver) may be configured to transmit and/or receive NIR radiation at wavelengths in said ranges. Correspondingly, also the NIR receiver may be configured to receive NIR light at such wavelengths. Also, the second NIR transceiver may be configured to transmit and/or receive NIR radiation at wavelengths in said ranges.

The reasoning behind these ranges is as follows: For a multi-chamber leadless pacemaker application, blood is the dominate tissue medium between the LP devices, and therefore the specific NIR frequency should be chosen to minimize the opacity of blood. As mentioned above, deoxygenated blood has an NIR absorption coefficient of 0.4 to 11 cm$^{-1}$ (depending on wavelength), and oxygenated blood has an absorption coefficient of about 1.7 to 7 cm$^{-1}$ (depending on wavelength). For deoxygenated blood, the lowest absorption coefficient (~0.4) occurs at a wavelength of about 1,100 nm. (This can be seen in FIG. 1 of Jacques, "Optical properties of biological tissues: a review", Phys. Med. Biol. 58 (2013) R37-R61, by conservatively extending the trend line of measured deoxygenated blood). Note that at wavelengths above ~1,100 nm, the absorption coefficient of the water content starts to dominate the overall absorption coefficient of blood (below this frequency the blood pigment dominates), and because of that the absorption coefficient at 1,100 nm is just slightly higher than water. Therefore, the optimal wavelength for, e.g., a dual chamber pacer (communicating RA to RV, both in the right side of heart) is ~1,100 nm. At such a frequency, the surviving fraction of light over 5 cm distance would be (from Equation 1 above) 13.5%. Of course, in addition to absorption the light received would also decrease by the inverse square law due to scattering causing the light to spread out in all directions as it moves away from the source. However, for left-sided heart operation (as in a LV to RV link), the NRI light must primarily cross the LV blood, which is oxygenated. This turns out to be more challenging for NIR communication. There are two minima in the graph of absorption coefficient vs. frequency for oxygenated blood in the NIR wavelengths, one at approximately 700 nm (absorption coefficient ~1.7) and a second one which is slightly higher at about 1,100 nm (absorption coefficient ~1.8). Since it would be inconvenient to have different frequencies of operation for communication in different chambers, in a preferred embodiment, the communication system operates at a wavelength of ~1,100 nm. At this frequency the surviving fraction of light over a 3 cm distance (from Equation 1) would be ~0.5%. This is more challenging to work with compared to the surviving fraction of light on the right side of the heart, but it is still workable (it just takes more receive power to amplify the signal).

In an embodiment, the NIR transceiver and/or the NIR receiver comprises a photo detector, e.g., in the form of a photo diode that is configured to sense NIR light in a wavelength range used for the communication. Further, in an embodiment, the (first or second) NIR transceiver comprises a transmitter portion with an NIR source (e.g. an NIR LED, LED—light emitting diode) configured to emit NIR light in a wavelength range used for the communication.

In this context, it should be noted that minimal size is an important design concern for most implantable medical devices, in particular for leadless pacemakers, and therefore it is preferable that any communication system be made of physically small components. Surface mount LEDs and photo detectors are readily available in the NIR window frequencies, e.g., in 0805 packages, and some parts are even available in smaller 0603 and 0402 packages. These have been developed for IrDA communication applications such as television remotes (IrDA is an acronym for Infrared Data Association). For example, Vishay Semiconductors VSMB1940X01 is a commercially available surface mount IR emitter centered on ~950 nm in an 0805 package (2 mm by 1.25 mm, and 0.85 mm high). Vishay Semiconductors also makes TEMD7100X01, which is a commercially available surface mount photodiode (receiver element) centered on light at ~950 nm which is also available in an 0805 package. SFH 4053 made by OSRAM Opto Semiconductors is an example of an infrared emitter at 850 nm arranged in a 0402 package. For the presently preferred operation with light centered at 1,100 nm, custom components (i.e., dedicated NIR LEDs and/or dedicated NIR photo diodes) may be produced, wherein the dies may be fit, for example, in a 0805 or smaller package consistent with implants size constraints.

In an embodiment, the housing(s) of the implantable medical device(s) may (each) comprise a glass window for letting pass through the NIR radiation. For example, the glass window may be hermetically sealed with the surrounding material of the housing. For example, the main material of the housing(s) may be titanium. Titanium is largely opaque to NIR frequencies, so a window is needed in the housing to allow NIR light to travel through. Hermetic glass to metal seals are a well-known technology, and can be used to incorporate a small glass window into an implantable medical device while keeping the device housing hermetic. NIR light will pass through most glass mixtures with minimal attenuation (longer wavelength IR is generally blocked by glass, but not NIR).

In a system having two or more implanted components that communicate among each other based on NIR, several or each of the components may comprise a housing having a window for letting pass through NIR light, as described above. In this context, it should be noted that it is not necessary for the NIR source to be line of sight with the NIR detector of the implant being communicated with. This is important, as the device (e.g., LP devices) can be implanted in any orientation with respect to one another. The glass windows can actually be facing completely away from each other and this communication scheme will still work. This is because the scattering coefficient of blood in the NIR window is relatively high, namely, at about 450 to 850 $cm^{-1}$, depending on the exact frequency (cf. Friebel et. al. "Influence of oxygen saturation on the optical scattering properties of human red blood cells in the spectral range 250 to 2,000 nm", J. of biomed. Optics 14 (2009)). This high amount of scattering means that photons arrive at the detector (NIR transceiver or NIR receiver) coming from all directions after scattering. Due to scattering, light spreads out from the transmitter like the glow around a street lamp on a misty day. Note that tissue overgrowth of the glass window is also not a concern because NIR light easily penetrates soft tissues, as already mentioned.

Care must be taken to design the NIR optical communication to be extremely low power consuming, e.g., for use in a LP system. This is because LP devices must last for 8 or more years on a single very small battery (typically <0.7 cc). The challenge of coordinating timing among multiple LP devices (e.g., one in the right atrium (RA) and one in the right ventricle (RV)) is that the LP devices must be watching for a signal at a very high duty cycle. This is because an intrinsic event (such as a premature ventricular contraction—PVC) may be detected at any time by an LP device in one chamber and then needs to be communicated to an LP device in another chamber.

In an embodiment, the receiver elements (e.g., the (first) NIR receiver and the NIR receiver (or second NIR transceiver)) are always on watching for a signal. In order for an LP device to always watch for a signal, and for it to have at least an 8 year longevity on a tiny battery (<200 mAh), and for the NIR receive system to take less than 10% of the overall battery capacity, the average current consumption of the NIR sensing system must be preferably <300 nA. For such a circuit to be practical, it may be advantageous that the NIR transmit source is as bright as possible (because unlike the receiver, the transmitter is not always on). A bright transmit pulse may be achieved by using relatively high (~100 mA), but very brief (just a few ns) instantaneous transmit current for each bit. It is well known that very brief light flashes are adequate for NIR communications. An example of this is the new gigabit per second IrDA communication protocol called Giga-IRtm, which sends bits in less than a nanosecond across its NIR link. This means that the average power required to transmit can be dramatically reduced by using such very brief NIR source pulses.

In a preferred embodiment, an NIR source (such as an NIR LED) is powered by discharging a small tank capacitor through the NIR source. The tank capacitor is then slowly recharged in between bits by a charge pump. This allows the instantaneous power driving the NIR source to be quite high (e.g., ~100 mA) while still maintaining a relatively small average transmit current draw from the battery, e.g., of just a few 100 nA.

Further, in an embodiment, on-off keying (OOK) modulation is used for the NIR signal(s). OOK modulation only turns on the NIR source for approximately half the bits (either the logical "1" bits or the logical "0" bits). Since the NIR source dominates the power draw of the transmit circuitry, using OOK modulation roughly cuts the transmit power draw in half over other modulations techniques. In a variant, data whitening algorithms can be used to guarantee that the NIR source is turned on for only half the bits. To improve the interference immunity of the NIR detector, a band pass filter designed around the OOK bit frequency can be used to reduce the effective noise and interference bandwidth.

In other embodiments, pulse position modulation (PPM) may be used for bit encoding within the NRI signal. PPM has the advantage that multiple data bits can be sent with a single pulse, which saves even more transmit power.

In an embodiment, the first implantable medical device is configured as a shallow implant medical device configured to be positioned subcutaneously. The first implantable medical device may thus fulfill the function of a subcutaneous implantable hub, which can take, for example, the form of a BioMonitor™ made by Biotronik. For example, the implantable hub can communicate with an LP device or a group of LP devices via the NIR communication link. Thus, the implantable hub may, for example, process and coordinate pacing timing, store histograms and E-grams recorded from the patient, and/or it can use RF telemetry to talk to a remote monitoring infrastructure.

For example, a Body Area Network (BAN) system may thus be formed, which comprises one hub device which is capable of both transmit and receive NIR signals and one or more LP devices which may be receive only (or also transmit and receive).

In another embodiment, the first implantable medical device and/or the second implantable medical device may be an implantable sensor (e.g., a pressure sensor) or a loop recorder.

In another embodiment, the system further comprises an external device configured to communicate with the first implantable medical device and/or the second implantable medical device via NIR optical communication. The term "external device" shall designate a device that is not intended to be implanted in the patient's body. For example, the external device may be a clinician's programmer or a patient remote.

In accordance with this embodiment, NIR communication may be used for programming the first implantable medical device and/or the second implantable medical device externally. To this end, for example, an NIR transducer of the external device is placed against the skin, against the clothing, or even nearby the clothing, and optical communication is begun. Distances involved in programming the implanted device from an external device is generally greater than those involved in heart chamber to heart chamber communication, but the external device has the advantage that it can afford to use much more power to transmit high intensity NIR light and more power for a higher gain receiver. The higher power available to the external device largely offsets the increased tissue attenuation at the greater distance (e.g., 8 cm from the external device to an LP device as opposed to 5 cm from an RV located LP device to an RA located LP device).

Hence, in this embodiment, the NIR communication link is used for communication between an external device (e.g., a clinician's programmer) and one or more implantable devices such as one or more LP devices. For example, in this embodiment, the external device may contain a small wand with the NIR transducers arranged on it. The wand may be designed to be placed directly on the patient's skin in proximity to the implant(s) for communications.

In a variant embodiment, the first implantable medical device and/or the second implantable medical device (e.g., an LP device) goes from a low power mode (e.g., a sleep mode) into a higher power receive mode (with higher gain) when communicating with the external device. The first implantable medical device and/or the second implantable medical device can afford to do this because it talks to an external device, such as a clinician's programmer, much less frequently than it communicates to other implanted devices, e.g., LP devices to coordinate pacing timing (e.g., once every few months as opposed to once every second).

In a further embodiment, the first or second implantable medical device is configured as a shallow implant medical device (such as the BioMonitor™ mentioned above), which utilizes NIR communication with an off-the-shelf external device (e.g., a clinician's programmer or a patient remote) and/or with one or more LP devices. The NIR wavelength selection may be optimized based on the use model at hand. For example, a wavelength between 850-950 nm can be used such that an off-the-shelf NIR emitter can be attached to a smartphone with custom designed software that controls the OOK sequence of the NIR emitter. A low cost silicon photodiode or photocell can be used in the optical detection circuitry of the shallow implant medical device.

In an embodiment, the first implantable medical device and/or the second implantable medical device (each) comprises an optical lens configured to focus an NIR signal that has been transmitted by the transceiver and/or an NIR signal that is to be received by the receiver/transceiver. This may be advantageous especially in case the first implantable medical device and/or the second implantable medical device is configured as a shallow implant medical device, as described above. For example, such a shallow implant medical device may comprise a header portion including said optical lens. An NIR optical lens co-designed with the header portion can greatly improve the optical efficiency of the system by focusing the received or transmitted NIR signal. The size and shape of the lens may depend on the optical properties of the material used for the header portion. An optical filter may also be provided in the header.

According to a second aspect of the present invention, another system is provided. The other system comprises an implantable medical device having an NIR receiver; and an external device having an NIR transmitter. The external device is configured to transmit to the implantable medical device at least one of an NIR wakeup signal; and an NIR key delivery signal including a cybersecurity key.

The implantable medical device may be a leadless pacemaker device, a loop recorder (shallow implant medical device), or an implantable pulse generator configured to provide electrical stimulation, e.g., for Neuro therapy.

Hence, in accordance with the second aspect, for example, a unidirectional NIR communication may be used for waking up a relatively high power transceiver and/or for delivering authentication/encryption message from an external device to a shallow implant medical device such as a BioMonitor™ (or any other implantable devices). In this way, the power efficiency and security of RF communication can be greatly improved. The external device in this embodiment can be, for example, a patient remote, a physician's programmer, or similar device. One advantage of waking up using the optical system is that it can be much lower power than other methods.

In this context, it should be noted that sunlight has significant energy in the NIR range. A sizeable portion of this energy (particularly above 950 nm wavelength) is filtered out by the atmosphere, but sunlight reaching the earth's surface still contains energy in the NIR range. Since some devices are implanted deep in the body, most NIR light from extra body sources such as sunlight is absorbed by the body tissue; however, some may still get through. To make sure that this does not wake up the implantable medical device's communication system too frequently, the wake up signal in a preferred embodiment is a multi-bit (e.g., 16-bit) sequence. Once wakeup is achieved, a handshake with cyclic redundancy check (CRC) may be exchanged to make sure the wakeup is intentional, and not due to a randomly modulated noise source such as sunlight. If the handshake is not successful, the wakeup is considered a false wakeup and the implantable medical device quickly goes back to a low power state.

In one embodiment, the optical NIR link is used as a secure side-band for exchanging cyber-security keys between the implantable device and the external device. The optical NIR link is ideal for exchanging keys because it is relatively short range compared to RF far-field telemetry and hence only works in close proximity to the patient.

Further, in an embodiment, a pseudo noise (PN) spreading sequence or other block code can be used for the NIR communication to spread each transmit data bit into multiple transmit symbols. At the receiver, the known PN sequence or block code can be used to combine multiple symbols into single data bit to improve the receiver sensitivity. For example, the external device may comprise a low power optical transmitter and receiver that utilize a PN sequence or a forward error correction (FEC) code for spreading and/or de-spreading such that the external device can deliver a wakeup request and/or a secret shared key to one or multiple implants via NIR without interference and at enhanced sensitivity.

According to a third aspect, a leadless pacemaker device is provided, which is configured to provide intracardiac pacing. The leadless pacemaker device comprises an NIR transceiver. The leadless pacemaker device may further comprise a housing. The NIR transceiver may be arranged in or at the housing. For example, one or more LP devices of the third aspect may be used as the first and/or second implantable medical device(s) and/or as the first or second LP devices referred to above in connection with the first and second aspects of the present invention. Hence, what has been explained above with regard to those devices, may also apply to the LP device of the third aspect in some embodiments, and vice versa.

In one embodiment, the LP device of the third aspect comprises a control circuitry configured to instruct the NIR transceiver to emit an NIR probe signal and to control the intracardiac pacing in dependence on a sensed NIR signal received by the NIR transceiver in response to the NIR probe signal. The sensed NIR signal may be a backscattered or reflected NIR signal. For example, the sensed NIR signal may be an NIR intensity.

For example, measuring the NIR light backscattered to the LP device that transmitted it may yield a signal with a component proportional to an instantaneous atrial or ventricular volume (depending on the location of the LP device). Using the optical transmitter and receiver in this mode relies on the relatively high scattering coefficient of blood (about 450 to 850 cm$^{-1}$) in the NIR window. By measuring the chamber volume (particularly the ventricle volume), even a single chamber LP device can obtain all sorts of useful timing information about the cardiac cycle. For example, in this way, a single chamber ventricular LP device may sense the atrial kick and use this input to provide VDD therapy. In this example, the timing of the atrial kick allows the ventricular LP device to provide for an atrial-ventricular (A/V) synchronous pacing in the ventricle.

A fourth, fifth, and sixth aspect refers in each case to operating methods that are related to the first, second, and third aspects described above, respectively.

Correspondingly, the fourth aspect relates to a method for operating a system. The system comprises a first implantable medical device comprising an NIR transceiver; and a second implantable medical device comprising an NIR receiver. The method comprises: transmitting an NIR signal by means of the NIR transceiver; and receiving the NIR signal by means of the NIR receiver. The system may be formed in accordance with any embodiment disclosed herein, in particular in accordance with the embodiments of the first aspect.

The fifth aspect relates to a method for operating a system. The system comprises an implantable medical device having an NR receiver and an external device having an NIR transmitter. The method comprises: transmitting, by means of the NIR transmitter, at least one of an NIR wakeup signal and an NIR key delivery signal including a cybersecurity key; and receiving the NIR wakeup signal and/or the NIR key delivery signal by means of the NIR receiver. The system may be formed in accordance with any embodiment disclosed herein, in particular in accordance with the embodiments of the second aspect.

In an embodiment in accordance with the fifth aspect, the implantable medical device switches from a low power receive mode to higher power receive mode in response to receiving the NIR wakeup signal. For example, a higher power communications subsystem of the implantable medical device may thus be woken up by means of a secure NIR based out of band communication.

The sixth aspect relates to a method for operating a leadless pacemaker device for providing for an intracardiac pacing. The method comprises: emitting an NIR probe signal from the leadless pacemaker device; and controlling the intracardiac pacing in dependence on a sensed (e.g., backscattered or reflected) NIR signal received by the NIR transceiver in response to the NIR probe signal. The use of sensed NIR light offers a new cardiac sensing modality which may be used for an optimized control of, e.g., a VDD pacing. Generally, this sensing modality may be used for measuring changes in cardiac volume, which has many potential applications in connection with implantable cardiac devices.

In an embodiment of the sixth aspect, the leadless pacemaker device is a ventricular leadless pacemaker device (e.g., a leadless pacemaker device which is implanted in a ventricle) and the method comprises: sensing an atrial kick by emitting the NIR probe signal and receiving the sensed NIR signal; and providing an A/V synchronous pacing in dependence on the sensed atrial kick.

In accordance with the different aspects of the present invention explained above, a unidirectional or bidirectional NIR communication may be used for a variety of use cases in connection with LP systems. In particular, this optical solution enables flexible unidirectional and bidirectional communication when one (or more) side of the communication is extremely power sensitive. For example, bidirectional NIR communication may be best suited for supporting a synchronization between multi-chamber leadless pacemaker (LP) devices, whereas a unidirectional NIR communication may allow for a wakeup or security key delivery from an external device to an implanted device. Those skilled in the art will appreciate that hybrid configurations which include both bidirectional and unidirectional NIR communication nodes are also possible and may enable, for example, a seamless integration of external devices (e.g., clinician's programmers or patient remotes), BioMonitor™ devices and LP devices.

All embodiments of the described systems and devices can be combined in any desired way and can be transferred in an analogous manner to the described methods, and vice versa.

Additional features, aspects, objects, advantages, and possible applications of the present invention will become apparent from a study of the exemplary embodiments and examples described below, in combination with the Figures, and the appended claims.

DESCRIPTION OF THE DRAWINGS

The various features and advantages of the present invention may be more readily understood with reference to the following detailed description and the embodiments shown in the drawings.

DETAILED DESCRIPTION

In the following, embodiments of the present invention shall be described in detail with reference to the drawings.

It is to be noted that the embodiments are not limiting for the present invention, but merely represent illustrative examples.

Figure 1A:
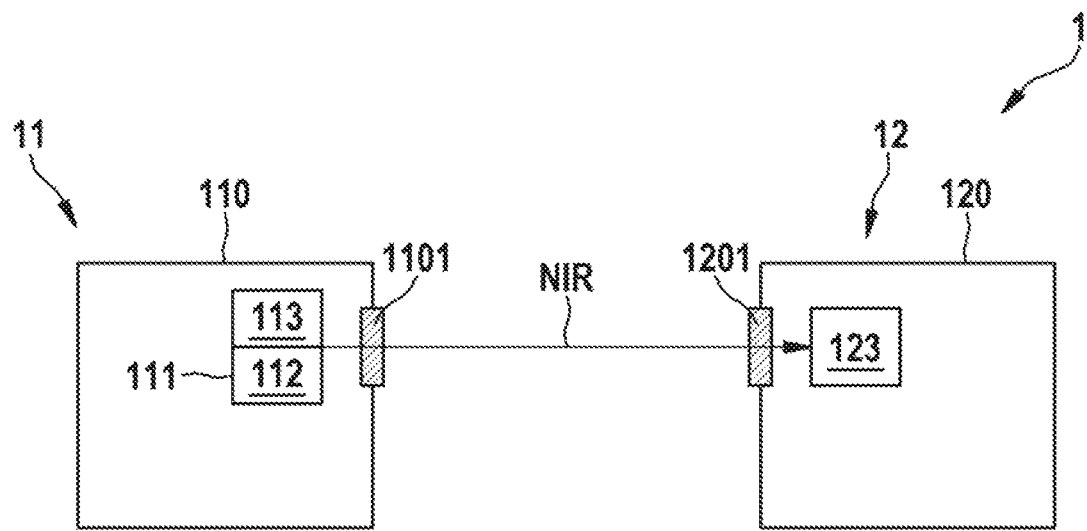
FIGS. 1A-1C each show a schematic block diagram of an LP system in accordance one or more embodiments.

FIG. 1A shows a schematic block diagram of a leadless pacemaker (LP) system 1 in accordance with one or more embodiments. The LP system 1 comprises an implantable medical device 11 and a first LP device 12. The first LP device 12 is configured to provide intracardiac pacing when implanted within a heart chamber of a patient.

The implantable medical device 11 may be, for example, a second LP device configured to provide intracardiac pacing. For example, in that case, the first LP device 12 and the second LP device 11 may form a part of a multi-chamber LP system 1, wherein the first LP device 12 and the second LP device 11 may be implanted in different chambers of the patient's heart (e.g., in a right ventricle (RV) and in a right atrium (RA), respectively).

Alternatively, the implantable medical device 11 may be, for example, a shallow implant medical device serving as a subcutaneous hub that communicates with one or more LP devices 12 and/or with an external device 13 (not illustrated in FIG. 1A, refer to FIG. 1B) of the LP system 1. Such a subcutaneous implantable hub 11 may, for example, take the form of a loop recorder (e.g., one of Biotronik's BioMonitor™ products), which may be configured to process and coordinate pacing timing, store histograms and E-grams recorded from the patient, and/or use RF telemetry to communicate with a remote monitoring infrastructure.

The implantable medical device 11 comprises a housing 110 and an NIR transceiver 111 arranged therein. Similarly, the first LP device 12 comprises a housing 120 and has an NIR receiver 123 arranged inside the housing 12. In one embodiment, the NIR receiver 123 is comprised by an NIR transceiver. Hereby, bi-directional telemetry between the two LP devices 11, 12 can be provided to coordinate pacing timing. The NIR receiver 123 of the first LP device 12 is configured to receive an NIR signal transmitted by the NIR transceiver 111 of the implantable medical device 11. For example, the NIR transceiver 111 comprises an NIR transmitter section 112 configured to transmit NIR light in a certain wavelength range, and the NIR receiver 123 may be configured to receive NIR light in that wavelength range. The wavelength range may be, for example, from 1000 nm to 1200 nm, such as from 1050 nm to 1150 nm. In a preferred embodiment, and NIR communication between the implantable medical device 11 and the first LP device 12 takes place at a wavelength of about 1100 nm.

The NIR transmitter section 112 of the NIR transceiver 111 may comprise an NIR source, e.g., in the form of an NIR LED. Further, the NIR transceiver 111 may comprise an NIR receiver section 113. For example, the receiver section 113 comprises an NIR detector, e.g., in the form of an NIR photo diode.

For example, in case the implantable medical device 11 is a second LP device implanted in a different heart chamber then the first LP device 12, the first LP device 12 and the second LP device 11 may be configured to perform a heart chamber to heart chamber communication by means of the NIR transceiver 111 and the NIR receiver/transceiver 123. In this way, the first LP device 12 and the second LP device 11 may use a communication link based on modulated NIR light, e.g., for the purpose of synchronizing their pacing timing.

Figure 1B:
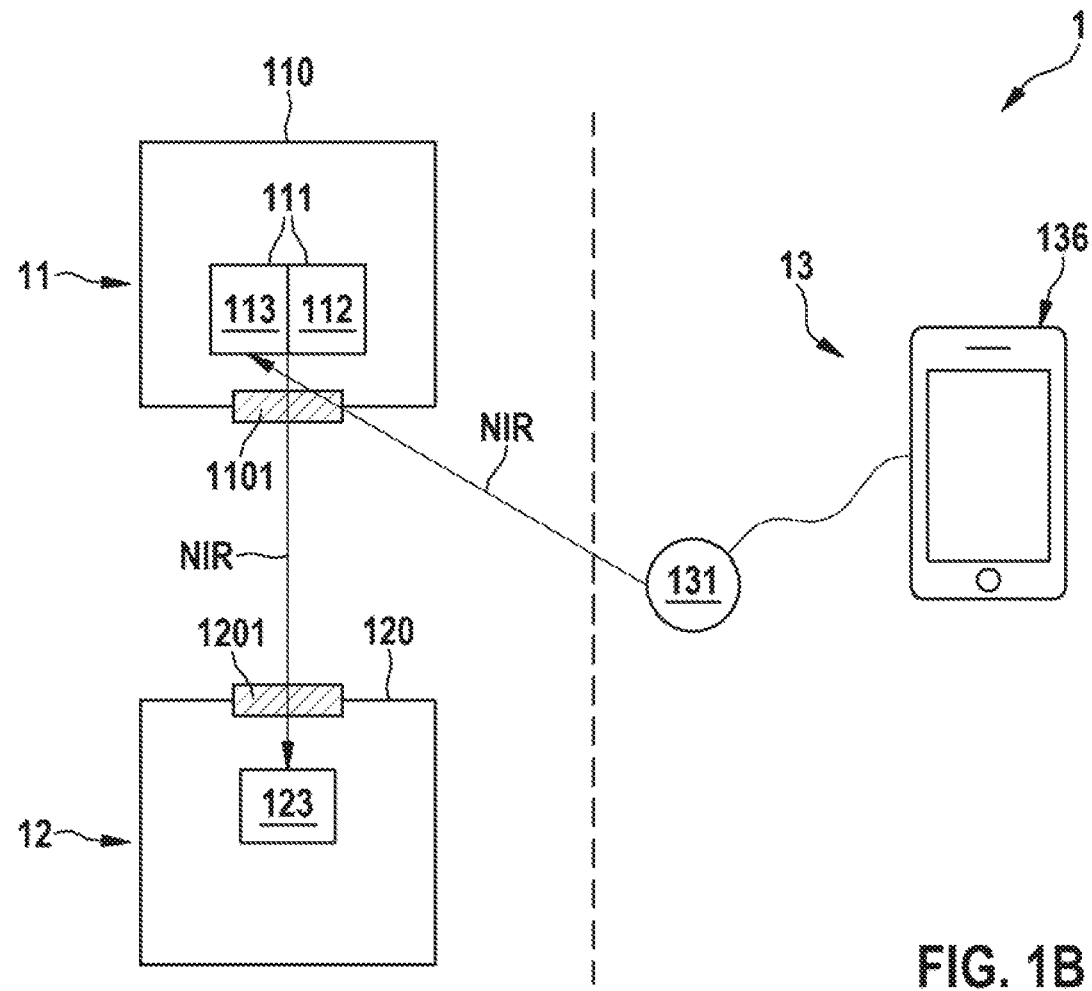

FIG. 1B schematically shows a block diagram of another embodiment, wherein the system 1 further comprises an external device 13, such as a clinician's programmer or a patient remote. As opposed to the implantable medical device 11 and the first LP device 12, the external device 13 is arranged external of the patient's body, which is schematically indicated in FIG. 1B by means of a vertical dashed line (symbolizing, e.g., the patient's skin). The external device 13 comprises a user interface 136, for example, in the form of a smartphone or an off-the-shelf clinician's programmer or patient remote. The user interface 136 is connected with an external NIR transmitter 131, which may be a customized, e.g., with respect to the preferable wavelength ranges mentioned above. The external device 13 is configured to communicate with the implantable medical device 11 by means of an NI R communication link, which comprises the external NIR transmitter 131 and the receiver section 113 of the transceiver 111 of the implantable medical device 11. For example, the external NIR transmitter 131 may be brought into the vicinity of the patient's skin for starting a communication with the implantable medical device 11.

In accordance with each of FIGS. 1A and 1B, the housing 110 of the implantable medical device 11 and/or the housing 120 of the first LP device 12 may comprise a glass window 1101, 1201 for letting pass through the NIR radiation used for the communication. For example, the housing's 110, 120 may be made of titanium, which is largely opaque to NIR light. The glass windows 1101, 1201 may be arranged in a hermetically sealed manner inside respective openings provided in the housings 110, 120. The transceiver 111 and the receiver/transceiver 123 may be arranged with respect to the respective glass window 1101, 1201 in such a way that the emitted and/or received NIR light may be pass through.

It should, however, be noted that while in the exemplary embodiment of FIG. 1A, the glass window 1101 of the implantable medical device 11 and the glass window 1201 of the first LP device 12 are precisely aligned with respect to one another, this is generally not necessary for the NIR communication. The reason is that the space between the implantable medical device 11 and the first LP device 12 may be filled with blood or bloody tissue, which has a relatively high scattering coefficient. Hence, NIR light emitted from the emitter section 112 of the transceiver 111 through the window 1101 will from there propagate essentially isotropically and will also be (partly) backscattered from the surrounding blood environment. As a result, that an NIR signal may be received by the receiver 123 of the first LP device 12 even if the window 1201 of the first LP device 12 does not directly face the window 1101 of the implantable medical device 11.

Figure 1C:
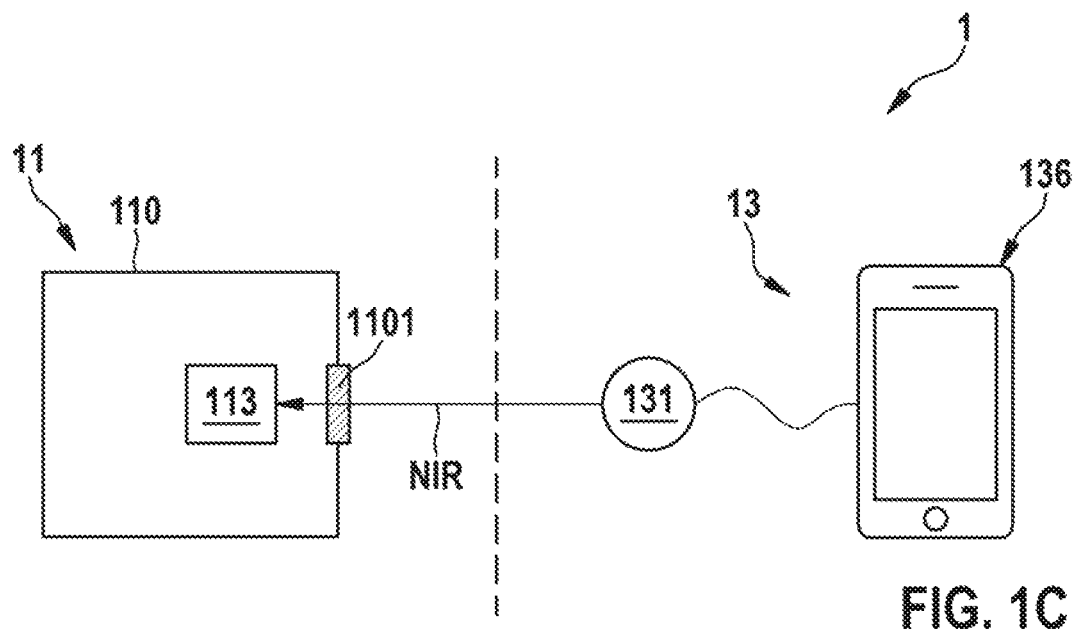

FIG. 1C schematically shows a block diagram of another exemplary embodiment of an LP system 1. The system 1 depicted in FIG. 1C comprises an implantable medical device 11 an external device 13, which communicates with the implantable medical device 11 via an NIR communication link. In accordance with FIG. 1C, the implantable medical device 11 may be an LP device having an NIR receiver 113 and being configured to communicate via an NIR communication link with external device 13. Regarding the external device 13, what has been stated above with reference to FIG. 1B may also apply to the external device 13 of FIG. 1C.

For example, the NIR transmitter 131 of the external device 13 may be configured to transmit to the implantable medical device 11 and NIR wakeup signal and/or an NIR key delivery signal that includes cybersecurity key. The implantable medical device 11 may receive a wakeup signal and/or the NIR key delivery signal by means of the NIR receiver 113. For example, the implantable medical device 11 may switch from a low power receive mode to a higher power receive mode in response to receiving the NIR wakeup signal. It should be noted that the receiver 113 of the implantable medical device 11 shown in FIG. 1C may be, for example, a receiver portion of an NIR transceiver, such as the NIR transceiver 111 shown in each of FIGS. 1A and 1B. The implantable medical device 11 may thus be configured to support unidirectional and/or bidirectional NIR communications with the external device 13 and possible also with further implantable devices, such as LP devices.

Figure 2:
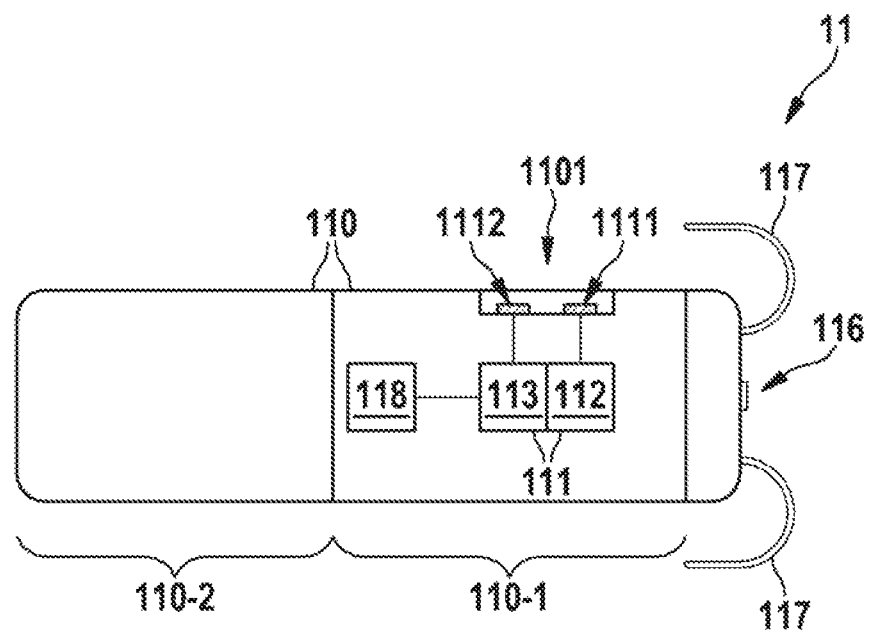
FIG. 2 shows a schematic view of an LP device in accordance with one or more embodiments.

FIG. 2 shows a schematic view of an LP device 11 in accordance with one or more embodiments. For example, in some embodiments, the leadless pacemaker device 11 of FIG. 2 may correspond to the implantable medical device 11 referred to above with regard to the systems 1 of FIGS. 1A to 1C. Further, in some embodiments, the LP device 11 of FIG. 2 may correspond to the first LP device 12 and/or the second LP device 11 referred to above in connection with FIGS. 1A to 1C. In other words, FIG. 2 may also be understood as an exemplary illustration of the first LP device 12 mentioned above.

As illustrated in FIG. 2, the leadless pacemaker device 11 comprises a housing 110, which has an electronics compartment 110-1 and a battery compartment 110-2. The battery compartment 110-2 of the housing 110 includes a battery (not illustrated in FIG. 2) as a power source for the pacing and the communication functions of the LP device 11. An NIR transceiver 111 is arranged in electronics compartment 110-1. The transceiver 111 comprises a transmitter section 112 including an NIR source 1111 (e.g., a NIR LED). Further, the transceiver 111 comprises a receiver section 113 with an NIR sensor 1112 (e.g., a photo diode). The NIR source 1111 and the NIR sensor 1112 are arranged behind a glass window 1101 that is integrated in a wall of the housing 110. For example, the glass window 1101 may be a hermetically sealed within the housing wall, which may comprise, for example, titanium. The electronics compartment 110-1 of the housing 110 further comprises a control circuitry 118 which is operably connected with the transceiver 111.

The LP device 11 further comprises a pacing electrode 116 that is configured to deliver pacing signals to the heart. Anchoring tines 117 are provided on the housing 110 so as to allow for a fixation of the LP device 11 inside a heart chamber.

For example, within a multi-chamber LP system 1, multiple LP devices 11 as illustrated in FIG. 2 may be provided in multiple chambers of the patient's heart. As already described above, a pacing timing may then be coordinated among the multiple LP devices 11, 12 by means of an NIR based communication.

In an embodiment, the control circuitry 118 of the LP device 11 is configured to instruct the NIR transceiver 111 to emit an NIR probe signal and to control the intracardiac pacing in dependence on a sensed (backscattered or reflected) NIR signal received by the NIR transceiver 111 in response to the NIR probe signal. In this manner, changes in cardiac volume may be sensed, which may be a valuable input for the control of the pacing. For example, the leadless pacemaker device 11 may be a (single chamber) ventricular leadless pacemaker device and the NIR probe signal in connection with the resulting sensed NIR signal (intensity) may be used to sense an atrial kick. Then, the control circuitry 118 may evaluate the received sensed NIR signal correspondingly and provide an A/V synchronous pacing in dependence on the sensed atrial kick.

Figure 3:
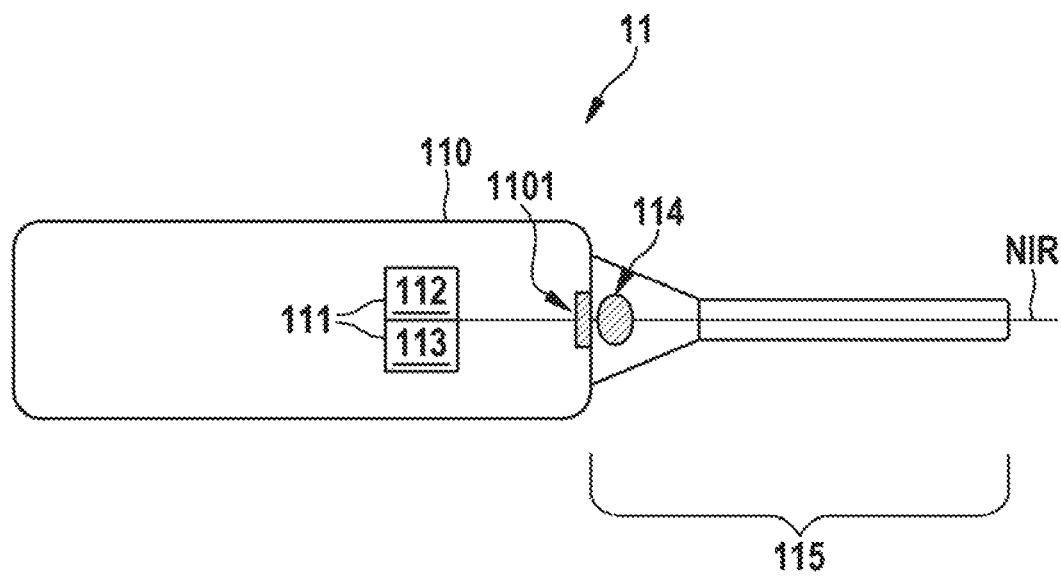
FIG. 3 shows a schematic view of an implantable medical device in accordance with one or more embodiments.

FIG. 3 shows a schematic of an implantable medical device 11 in accordance with some embodiments. For example, in some embodiments, the implantable medical device 11 of FIG. 3 may correspond to the implantable medical device 11 of an LP system 1 explained above with reference to one of FIGS. 1A to 1C.

Specifically, if the implantable medical device 11 of the LP system 1 is configured as a subcutaneous implantable hub that communicates with an external device 13 via either an NIR link (as shown in FIG. 3) or a far-field RF link, it may take the form as schematically and exemplarily illustrated in FIG. 3. In one embodiment, the hub communicates with one of more implants (e.g., leadless pacemakers) via an NRI optical link, but the hub communicates to an external device (e.g., a smartphone or a clinician programmer) via a far-field RF link. The reason is that the hub may have a larger battery than the implants, and is implanted at a much shallower depth in tissue, so it can much more easily use far-field RF to communicate.

The implantable medical device 11 of FIG. 3 comprises a housing 110 which includes a transceiver 111 having a transmitter section 112 as well as the receiver section 130. A glass window 1101 is provided in a wall of the housing 110 so as to let pass through incoming and/or outgoing NIR radiation. The implantable medical device 11 further comprises a header portion 115 that is configured for guiding the incoming and/or outgoing NIR light. Specifically, the header portion 115 comprises an optical lens 114 that is configured to focus an NIR signal that has been transmitted by the transmitter portion 112 and/or an NIR signal that is to be received by the receiver portion 113. In this way, the NIR based communication with an external device, such as the external device 13 illustrated in each of FIGS. 1B and 1C, may be facilitated. In another embodiment the optical lens 114 is achieved by shaping the glass window 1101 (adding a convex or concave curvature to its surface(s). In this embodiment the optical lens is the glass window.

Figure 4A:
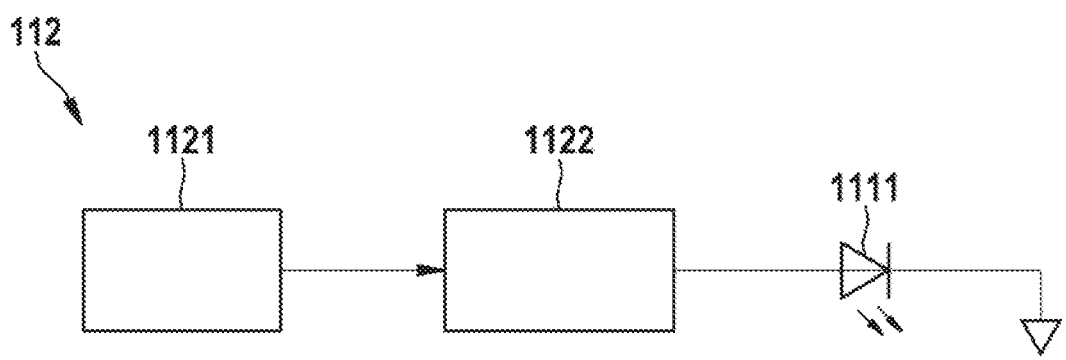
FIG. 4A shows a schematic block diagram of an NIR transmitter in accordance with one or more embodiments.

FIG. 4A shows a schematic block diagram of an NIR transmitter 112 which is suitable for enabling an NIR communication as described above. The NIR transmitter 112 of FIG. 4A may correspond, for example, to the NIR transmitter portion 112 of the NIR transceiver 111 of the implantable medical device 11 referred to above in connection with FIGS. 1A-3. The NIR transmitter 112 comprises an oscillator stage 1121. For example, the oscillator stage may be configured to generate an oscillating electrical signal at an oscillation frequency of about 1 kHz. Downstream of the oscillator stage 1121, a current driver stage 1122 is provided. In one embodiment, a modulation stage is arranged between the oscillator stage 1121 and the driver stage 1122. The modulation stage may be configured to modulate the oscillator output according to the data stream to be sent. The modulation stage may gate the oscillation signal on/off for bits 1 or 0. In other embodiments, the frequency of the oscillator could change between a 1/0 or the amplitude of the current driver stage could change to differentiate a 1 from a 0. For example, the current driver stage 1122 is configured in the form of a variable current driver which supports a current range from 0.1 A and 1 A. An NIR source 1111 is arranged downstream of the current driver stage 1122. The NIR source 1111 receives a current signal from the current driver stage 1122 and emits an NIR signal accordingly.

Figure 4B:
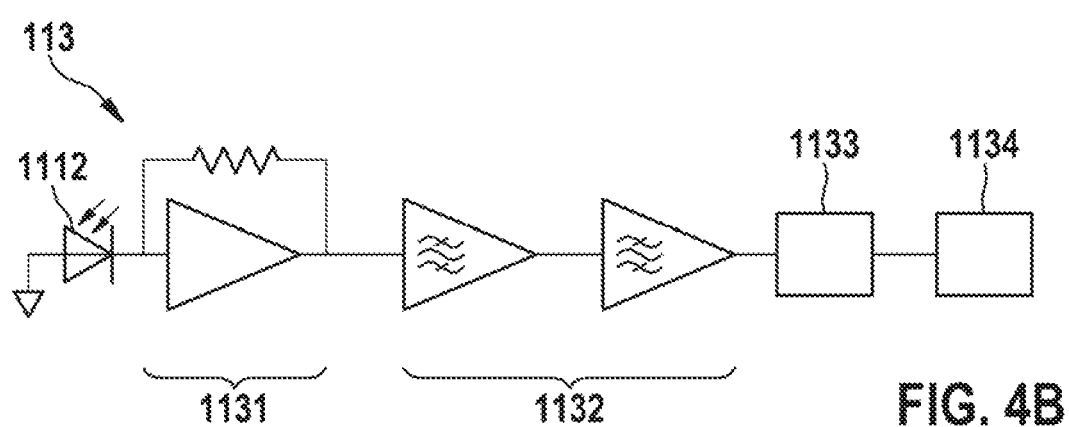
FIG. 4B shows a schematic block diagram of an NIR receiver in accordance with one or more embodiments.

FIG. 4B shows a schematic block diagram of an NIR receiver 113 which is suitable for enabling an NIR communication as described above. For example, in some embodiments, the NIR receiver 113 of FIG. 4B may correspond to the receiver section 113 of the NIR transceiver 111 of the implantable medical device 11 referred to above in connection with FIGS. 1A-3. Also the NIR receiver 123 of the first LP device 12 referred to above in connection with FIGS. 1A and 1B may be configured as schematically illustrated in FIG. 4A. The NIR receiver 113 of FIG. 4B comprises, as an NIR detector, an NIR sensor 1112. Downstream of the NIR sensor 1112, a transimpedance amplifier stage 1131 is provided. The transimpedance amplifier stage 1131 is followed by a demodulation stage 1132. One implementation of a demodulation stage that can be used to demodulate ASK encoded data is a band pass amplifier (as is shown in 1132). For example, the band pass amplifier 1132 may customized for a frequency of about 1 kHz at a Gain of G=25. Downstream of the band pass amplifier 1132, a signal detection stage and an indicator stage are provided.

Figure 5A:
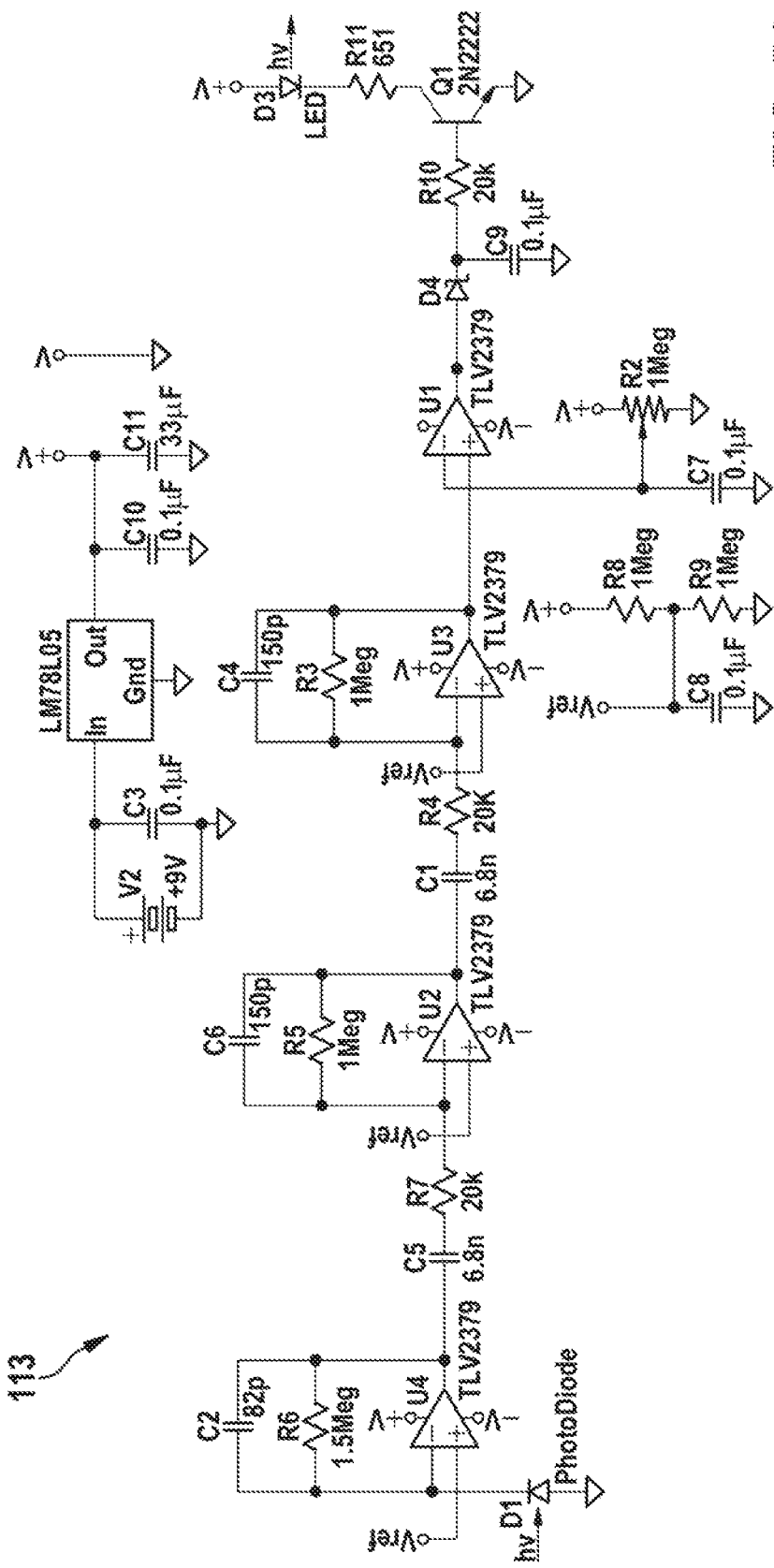
FIG. 5A shows a schematic switching circuit of an NIR receiver in accordance with one or more embodiments.
Figure 5B:
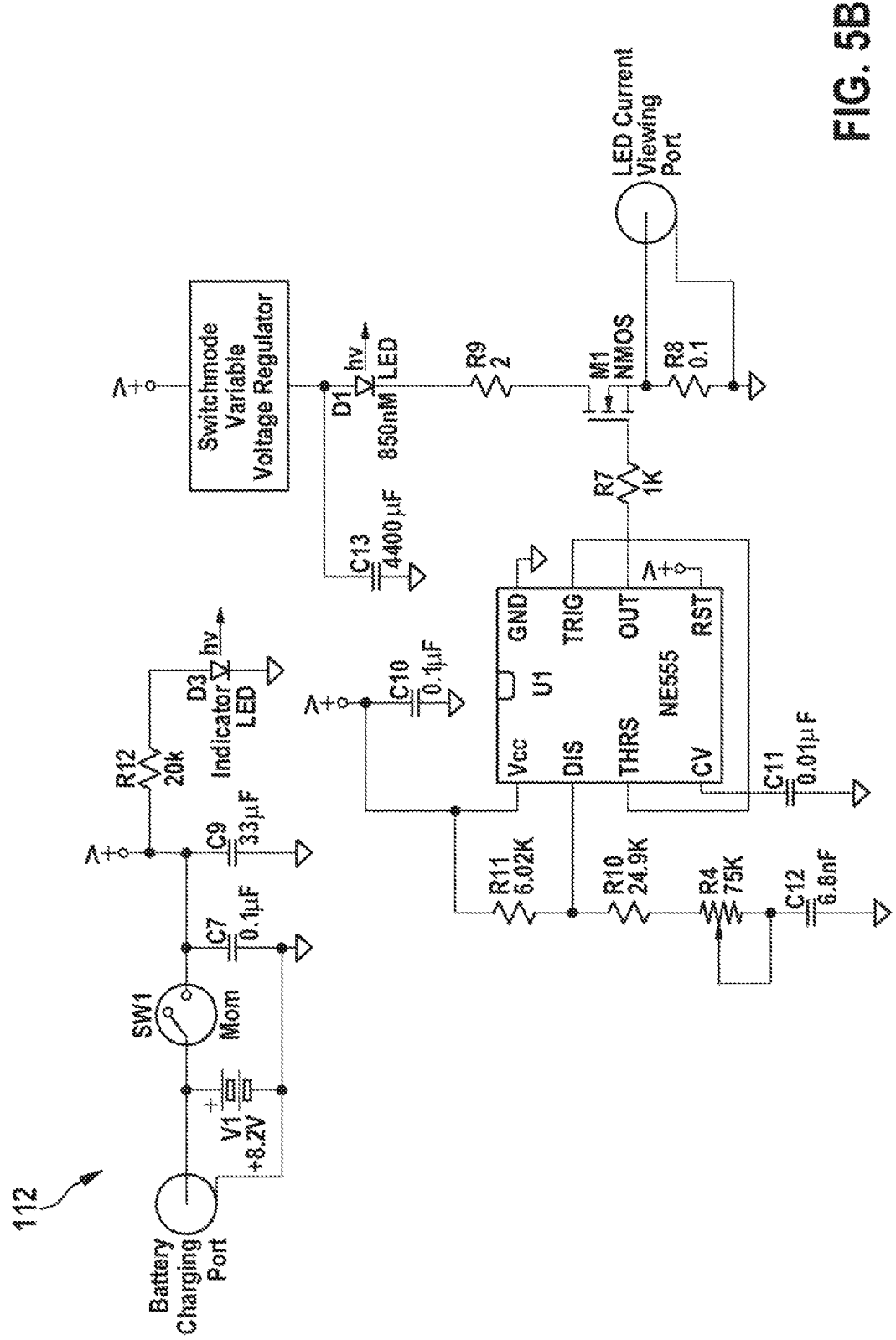
FIG. 5B shows a schematic switching circuit of an NIR transmitter in accordance with one or more embodiments.

FIGS. 5A and 5B show a switching circuit of an NIR receiver 113 and an NIR transmitter 112, respectively, which are suitable for enabling an NIR communication as described above.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Leadless pacemaker system
11 Implantable medical device
110 Housing
110-1 Electronics compartment
110-2 Battery compartment
1101 Glass window
111 NIR transceiver
1111 NIR source
1112 NIR sensor
112 NIR transmitter section
1121 Oscillator stage
1122 Current driver stage
113 NIR receiver section
1131 Transimpedance amplifier stage
1132 demodulation stage
1133 Signal detection stage
1134 Indicator stage
114 Optical lens
115 Header portion
116 Pacing electrode
117 Anchoring tines
118 Control circuitry
12 First leadless pacemaker device
120 Housing
1201 Glass window
123 NIR receiver
13 External device
131 NIR transmitter
136 User interface

We claim:

1. A system, comprising:
a first implantable medical device comprising an NIR transceiver; and
a second implantable medical device comprising an NIR receiver,
wherein the NIR receiver is configured to receive an NIR signal transmitted by the NIR transceiver, and
wherein the first implantable medical device is a first leadless pacemaker device configured to provide intracardiac pacing, wherein the first leadless pacemaker device comprises a first NIR transceiver.

2. The system of claim 1, wherein the second implantable medical device is a second leadless pacemaker device configured to provide intracardiac pacing, wherein the second leadless pacemaker device comprises a second NIR transceiver.

3. The system of claim 2, wherein the first leadless pacemaker device and the second leadless pacemaker device, when implanted in different heart chambers of a patient, are configured to perform a chamber-to-chamber communication by means of the first NIR transceiver and the second NIR transceiver.

4. The system of claim 1, further comprising an external device configured to communicate with the first implantable medical device and/or the second implantable medical device via NIR optical communication.

5. The system of claim 1, wherein the NIR transceiver is configured to transmit and/or receive NIR radiation at wavelengths in the range from 1000 nm to 1200 nm.

6. A method for operating a system, the system comprising:
a first implantable medical device comprising an NIR transceiver; and
a second implantable medical device comprising an NIR receiver;
wherein the NIR receiver is configured to receive an NIR signal transmitted by the NIR transceiver, and
wherein the first implantable medical device is a first leadless pacemaker device configured to provide intracardiac pacing, wherein the first leadless pacemaker device comprises a first NIR transceiver,
wherein the method comprises:
transmitting an NIR signal by means of the NIR transceiver; and
receiving the NIR signal by means of the NIR receiver.

* * * * *